United States Patent [19]
Baumann et al.

[11] Patent Number: 5,311,874
[45] Date of Patent: May 17, 1994

[54] METHOD FOR TACHYCARDIA DISCRIMINATION

[75] Inventors: Lawrence S. Baumann, Bloomington; David K. Swanson, Roseville; Douglas Lang, Arden Hills, all of Minn.

[73] Assignee: Cardiac Pacemakers, Inc., St. Paul, Minn.

[21] Appl. No.: 884,770

[22] Filed: May 18, 1992

[51] Int. Cl.$^5$ .......................................... A61B 5/0464
[52] U.S. Cl. ..................................... 128/705; 128/702
[58] Field of Search ................... 364/413.06; 128/702, 128/705, 703, 704, 696

[56] References Cited

U.S. PATENT DOCUMENTS

| | | | |
|---|---|---|---|
| 4,742,458 | 5/1988 | Nathans et al. | 128/702 |
| 5,090,148 | 2/1992 | Squires et al. | 128/702 |
| 5,161,539 | 11/1992 | Evans et al. | 364/413.06 |

OTHER PUBLICATIONS

Todd Cohen et al., "A Hemodynamically Responsive Antitachycardia . . . ", J. of Electrophysiology, vol. 2, No. 4, 1988, pp. 352-358.
Robert Throne et al., "A Comparison of Four New Time-Domain . . . ", Biomed. Engr. vol. 38, No. 6, Jun. 1991, pp. 561-570.
M. A. Tooley et al., "Recognition of Multiple Tachyarrhythmias . . . ", PACE, vol. 14, Feb. 1991, Part II, pp. 337-340.
D. Wyn Davies et al., "Detection of Pathological Tachycardia . . . ", PACE, vol 9, Mar.-Apr. 1986, pp. 200-208.
Gordon F. Tomaselli et al, "Morphologic Differences . . . ", PACE, vol. 11, Mar. 1988, pp. 254-262.
V. E. Paul et al., "Automatic Recognition of Venticular . . . ", PACE, vol. 14, Aug. 1991, pp. 1265-1273.

Primary Examiner—William E. Kamm
Assistant Examiner—Kennedy J. Schaetzle
Attorney, Agent, or Firm—Keck, Mahin & Cate

[57] ABSTRACT

A cardiac discrimination method in which feature values of a heart related signal (e.g., cardiac biopotentials) determined to be non-baseline are compared with feature values of a heart related signal determined to be normal baseline. The feature values are extracted on an event-basis (a periodically), for obtaining feature values of a complex. For each complex, the feature values form a sequence with the value having the largest absolute value for the sequence given special identity as a fiducial point. The normal baseline complexes' characteristic sequence and a non-baseline complex's sequence are aligned according to the fiducial points, and unoccupied positions on the ends of the sequences resulting from the alignment are filled with zeros to create normal baseline and non-baseline vectors. The similarity value and dissimilarity value of the normalized non-baseline vector with respect to the normalized normal baseline vector are determined. The type of tachycardia (VT or non-VT) and consequently the selection of appropriate therapy are determined by the location in a discrimination plane of a discrimination point, the coordinates of which are equal to the similarity and dissimilarity values. In addition, the location of a similarly generated hemodynamic discrimination point can be used to discriminate hemodynamically stable and unstable tachycardias based on the features derived from events in hemodynamic related signals. Furthermore, physiological indicators may be processed in a similar manner to determine an ideal rate at which the heart should be paced by a pacemaker.

22 Claims, 5 Drawing Sheets $$\left\{\begin{array}{l}\text{NORMAL BASELINE}\quad N_1, \overset{*}{N_2}, N_3, N_4 \\ \text{NON-BASELINE}\quad A_1, A_2, A_3, \overset{*}{A_4}, A_5 \\ \qquad\qquad\qquad\qquad\quad \wedge \\ \qquad\qquad\qquad\text{FIDUCIEL} \\ \qquad\qquad\qquad\text{POINT}\end{array}\right.$$

FIG.4

$$\left\{\begin{array}{l}\qquad\qquad\qquad\quad\text{ZERO FILL} \\ \text{NORMAL BASELINE VECTOR}\ \vec{N}=<0,0,N_1,\overset{*}{N_2},N_3,N_4> \\ \text{NON-BASELINE VECTOR}\ \vec{A}=<A_1,A_2,A_3,\overset{*}{A_4},A_5,0> \\ \qquad\qquad\qquad\qquad\qquad\qquad\quad \wedge\quad \text{ZERO FILL}\\ \qquad\qquad\qquad\qquad\qquad\text{FIDUCIEL}\\ \qquad\qquad\qquad\qquad\qquad\text{POINT}\end{array}\right.$$

FIG.5

METHOD FOR TACHYCARDIA DISCRIMINATION

RELATED APPLICATION

This application relates to commonly assigned U.S. patent application Ser. No. 07/884,563, filed on even date, and entitled METHOD AND APPARATUS FOR EVENT PROCESSING IN BIOLOGICAL APPLICATIONS.

BACKGROUND OF THE INVENTION

The present invention relates to a method for discriminating between tachycardias based on cardiac biopotentials, to a method for discriminating hemodynamically stable and unstable tachycardias based on cardiac signals, and to a method for controlling rate-adaptive pacing based on the simultaneous inputs of signals from multiple physiological sensors.

In particular, the present invention relates to a certain event-based algorithm for discriminating between tachycardias or for controlling rate adaptive pacing.

Event-based systems and methods are new to the field of implantable cardiac treatment systems. The aforementioned co-pending application relates to event-based processing techniques for tachycardia detection and to a method for discriminating between abnormal rhythms and normal sinus rhythm (NSR) using timing interval-binning and averaging, on an event basis.

Like the co-pending application, the invention of the instant application exploits the advantages of an event-based system, but is directed to a different event-based method for analyzing data related to cardiac function.

It is well known in the art that certain tachycardias are more life-threatening than other tachycardias. For example, it is known that ventricular tachycardia (VT) often leads to ventricular fibrillation if not treated, particularly when accompanied by abnormal hemodynamic activity. On the other hand, non-ventricular tachycardia (non-VT) generally does not lead to more threatening conditions. Examples of non-VT are supraventricular tachycardia (SVT) and sinus tachycardia (ST). The ability to distinguish the more threatening tachycardias from the less threatening ones is critical in preventing a more serious cardiac condition from developing, such as ventricular fibrillation. It is also desirable to eliminate unnecessary therapy. There are several methods, heretofore known, used for distinguishing between VT and non-VT.

One such algorithm is based upon rate-only. However, the difficulty with this algorithm lies in the fact that the rates of non-VT and VT can overlap. Therefore, it can be extremely difficult to determine the type of the tachycardia based solely on rate.

Another technique, known as A-V timing, compares the timing of atrial and ventricular biopotentials. While this method works better than the rate-only method, problems occur when the atrial and ventricular rates are equal. Specifically, when the ventricular rate is equal to the atrial rate, it is possible that the heart is in a junctional tachycardia, ST, or VT with retrograde 1:1 conduction. In addition, a drawback of this algorithm is its need for two leads for sensing.

Yet another known technique uses a probability density function (PDF) for discrimination on a morphological basis. This method performs well when differentiating narrow versus wide QRS complexes. However, this technique incorrectly identifies narrow monomorphic ventricular tachycardias and cannot be used with a patient with wide QRS complexes, due to preexisting bundle blocks or aberrant conduction, at rest.

In addition, algorithms are known which discriminate hemodynamically stable from unstable tachycardias by examining a single feature derived from cardiac signals (e.g., pressure, volume, or impedance). The majority of these methods rely on right heart measurements. However, any single feature derived from these measurements may not adequately reflect systemic hemodynamic conditions.

Furthermore, algorithms are known which control rate-adaptive pacing by examining a single feature (e.g., stroke volume, dV/dt, pre-ejection interval, minute ventilation, or activity) derived from physiological signals. However, single feature algorithms do not have the sensitivity and specificity required for precise physiologic pacing in all patients.

SUMMARY OF THE INVENTION

It is a primary object of the present invention to discriminate between ventricular tachycardia (VT) and non-ventricular tachycardia (non-VT) based on cardiac biopotentials and to select appropriate cardiac therapy.

It is another object of the present invention to select the appropriate cardiac therapy by discriminating between hemodynamically stable and unstable tachycardias based on cardiac signals.

It is a further object of the present invention to provide a method for controlling a pacing rate based on the simultaneous inputs of signals from multiple physiological sensors.

In one embodiment, the present invention is directed to a method for classifying in a broad sense, or discriminating in a more specific sense, harmful tachycardias and less harmful ones. A cardiac biopotential is sensed and processed to obtain a processed signal. The cardiac biopotential comprises a series of "complexes" which reflect cardiac electrical activity, and which may be non-constant in their frequency of occurrence (aperiodic). For each complex in the processed signal, the sequence of maximum positive and minimum negative values, termed feature values of the complex, are obtained, and the value with the largest absolute value is identified. This process is repeated on a patient for signal complexes determined to be baseline so that an accurate determination of the characteristic sequence of feature values of the complexes in a normal baseline signal can be obtained. Similarly, this process is performed once for each complex in a signal determined to be non-baseline.

The characteristic sequence of feature values of the complexes in a normal baseline signal and the sequence of feature values of a complex in a non-baseline signal are aligned by identifying the feature value with the largest absolute value in each sequence. This value is designated the fiducial point for the sequence. The characteristic normal baseline sequence and a non-baseline sequence are aligned so that the fiducial points in the two sequences coincide. Two m-dimensional vectors are then created from the aligned sequences by filling in the missing entries on the ends in either sequence with zeros. The value of m depends on the alignment of the two sequences and the number of zeros needed to fill the missing entries in each sequence. Thus, an m-dimensional normal baseline vector and an m-dimensional non-baseline vector are created.

The vectors are then normalized to the normal baseline vector by dividing each vector by the magnitude of the normal baseline vector. A discrimination plane is then defined by the two normalized vectors. Predetermined regions of the discrimination plane are used to classify the tachycardia and specify appropriate therapy. Specifically, the similarity value and the dissimilarity value of the normalized non-baseline vector with respect to the normalized normal baseline vector are computed. The similarity value is the projection of the normalized non-baseline vector onto the normalized normal baseline vector, which has unit length. The dissimilarity value is the projection of the normalized non-baseline vector onto the vector in the discrimination plane which has unit length and which is orthogonal to the normalized normal baseline vector.

The similarity and dissimilarity values are used to locate a point in a similarity-dissimilarity coordinate plane, also referred to as a discrimination plane. Certain regions in the discrimination plane are associated with certain tachycardias. These regions are predetermined by testing a population of patients. Thus, the location of the point defined by the similarity-dissimilarity values of a normalized non-baseline vector with respect to the normalized normal baseline vector classifies the non-baseline complex as a VT complex or non-VT complex. The accumulated classifications of the complexes in the non-baseline signal are used to classify the tachycardia as VT or non-VT so that appropriate therapy can be specified. The non-VT condition detected may be SVT, ST, or other tachycardias that are not classified as the more potentially harmful VT.

In a second embodiment, conditions or signals related to the hemodynamics of the heart are sensed and processed in a similar manner. The result is a hemodynamic discrimination point, the location of which in a hemodynamic discrimination plane is associated with the hemodynamic stability of the heart. Features derived from such signals may involve pressure, flow, volume, or impedance.

In a third embodiment, signals related to physiological conditions of the heart are sensed and processed in a similar manner. The result is a physiological discrimination point, the location of which in a physiological discrimination plane is associated with the appropriate pacing rate in a rate-adaptive pacing system. Features may include stroke volume, dV/dt, pre-ejection interval, minute ventilation, flow, and activity derived from simultaneous signals from multiple physiological sensors.

The above and other objects and advantages of the present invention will become more apparent when reference is made to the following description taken in conjunction with the accompanying drawings.

BRIEF DESCRIPTION OF THE DRAWINGS

FIG. 4 is a diagram illustrating the step of aligning the normal baseline and non-baseline sequences according to their fiducial points, in accordance with the discrimination algorithm of the present invention.

FIG. 5 is a diagram illustrating the step of creating normal baseline and non-baseline vectors by zero filling empty spaces on the ends of the sequences, in accordance with the discrimination algorithm of the present invention.

DETAILED DESCRIPTION OF THE DRAWINGS

Figure 1:
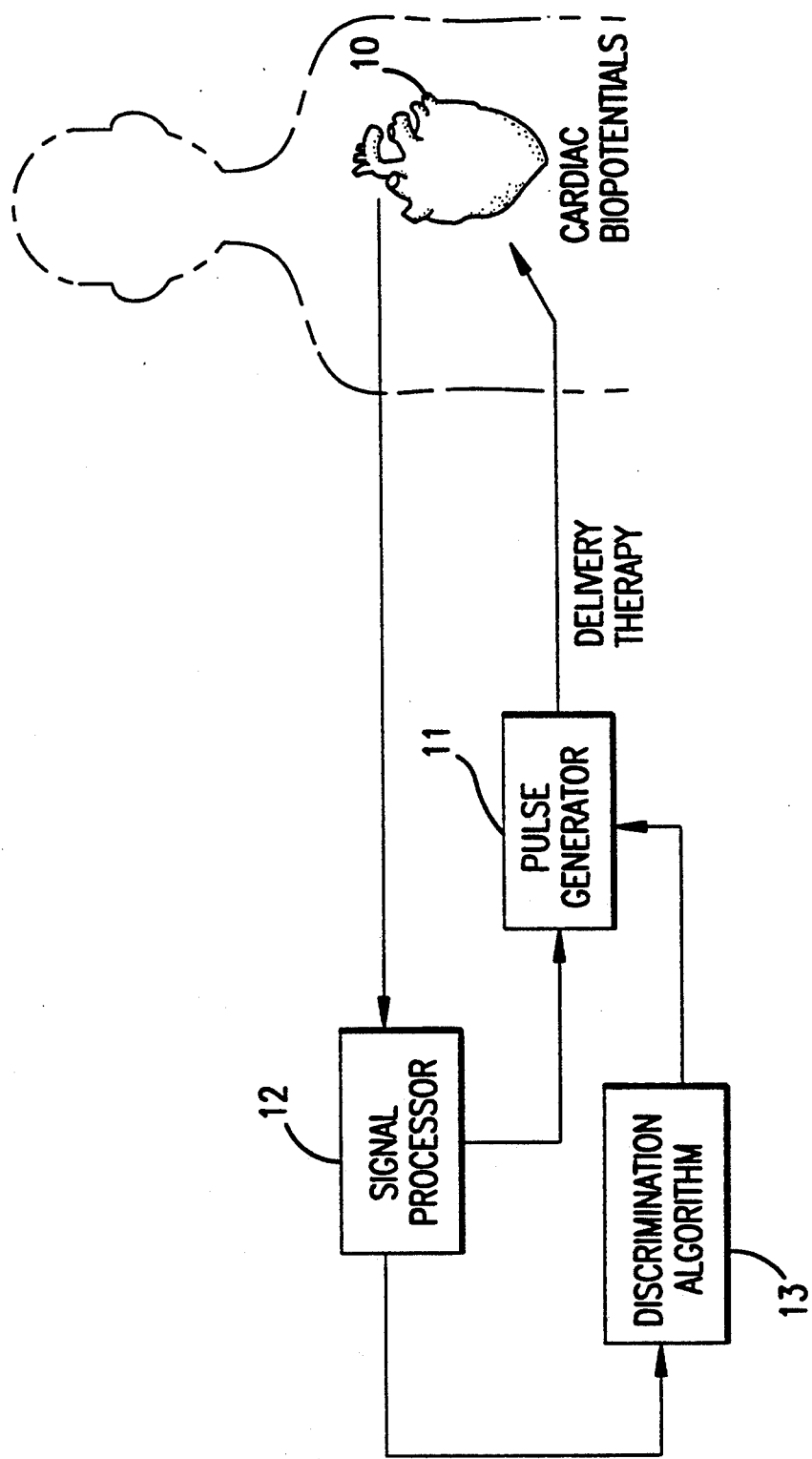
FIG. 1 is a block diagram generally illustrating the environment in which the algorithm of the present invention is used.

Referring first to FIG. 1, a particular environment in which the discrimination algorithm of the present invention is shown. Cardiac biopotentials are sensed from the heart 10 and fed to a signal processor 12, the purpose of which will be explained in further detail hereinafter. The output of the signal processor 12 comprises the input to the discrimination algorithm 13. The processed cardiac biopotentials are processed further by the discrimination algorithm and certain therapeutic measures are taken based on the results of the algorithm analysis. For example, a pulse generator 11 can be activated to shock the heart with a cardioversion/defibrillation pulse.

Figure 2:
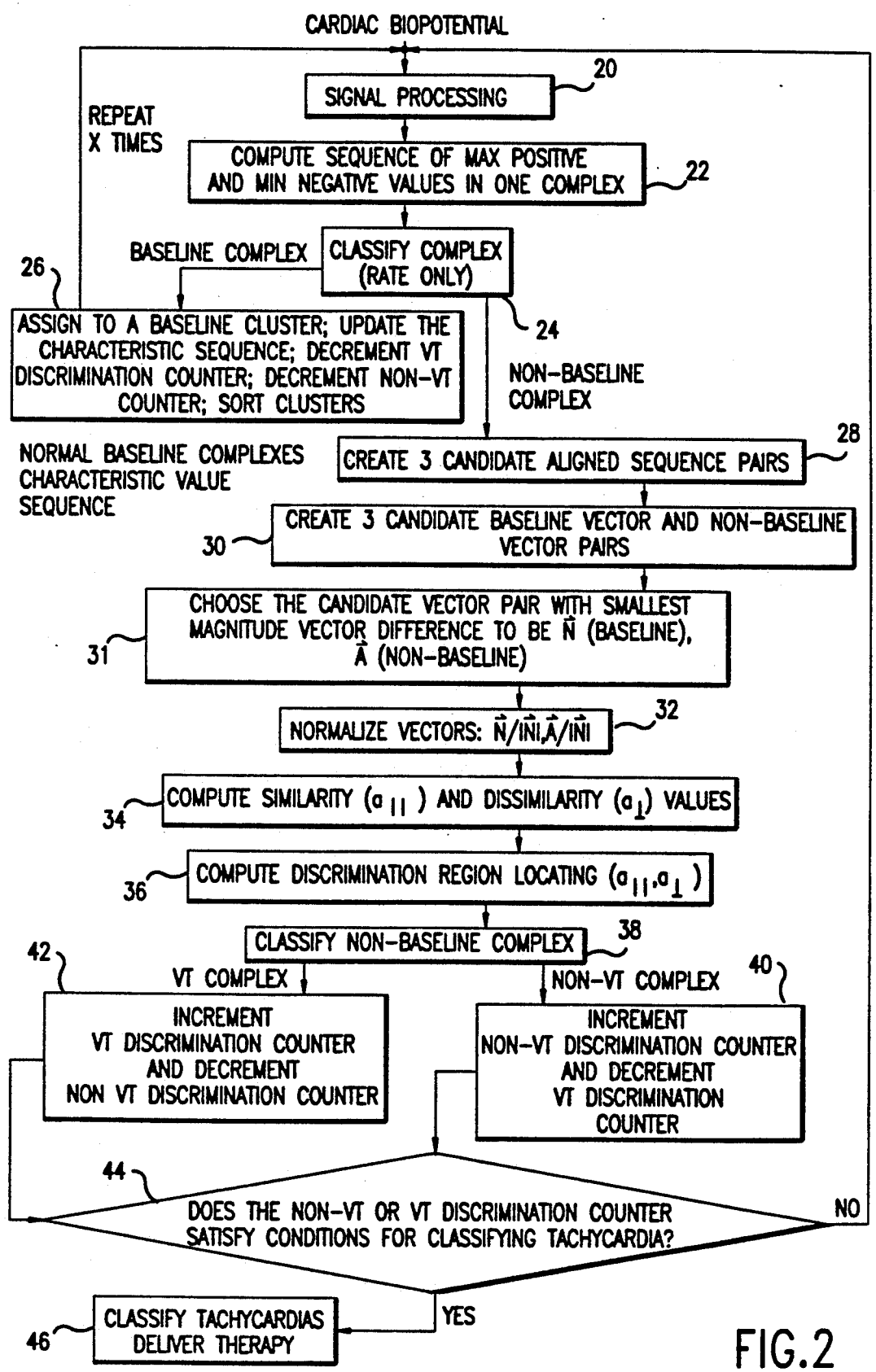
FIG. 2 is flow chart illustrating the discrimination algorithm for tachycardia discrimination, according to the present invention.

FIG. 2 illustrates the steps performed in the discrimination algorithm according to the present invention. Steps 20 and 22 are performed in order to obtain two sets of data. However, the following description is provided to explain in the abstract how these steps operate. The signal processing step 20 (performed by the signal processor 12) processes the input cardiac biopotential signal.

Figure 3A:
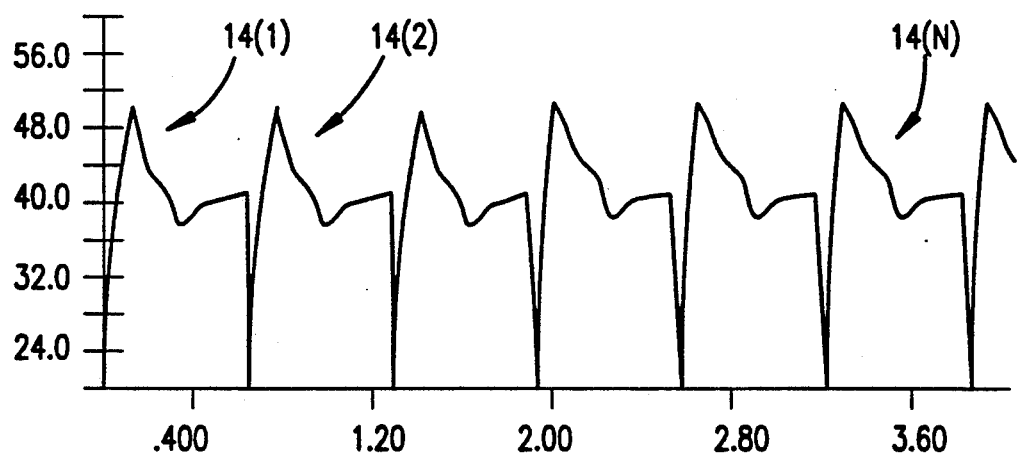
FIGS. 3A–3C are graphical diagrams illustrating an initial processing step of the discrimination algorithm of the present invention.
Figure 3B:
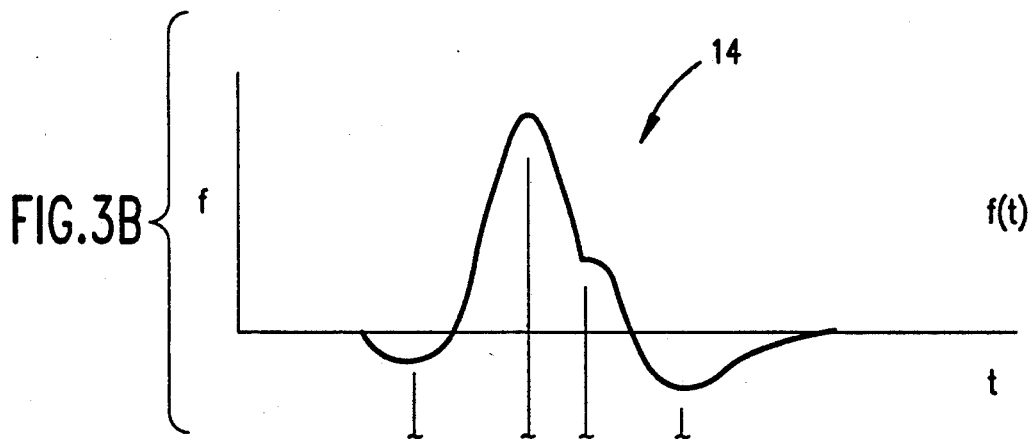
Figure 3C:
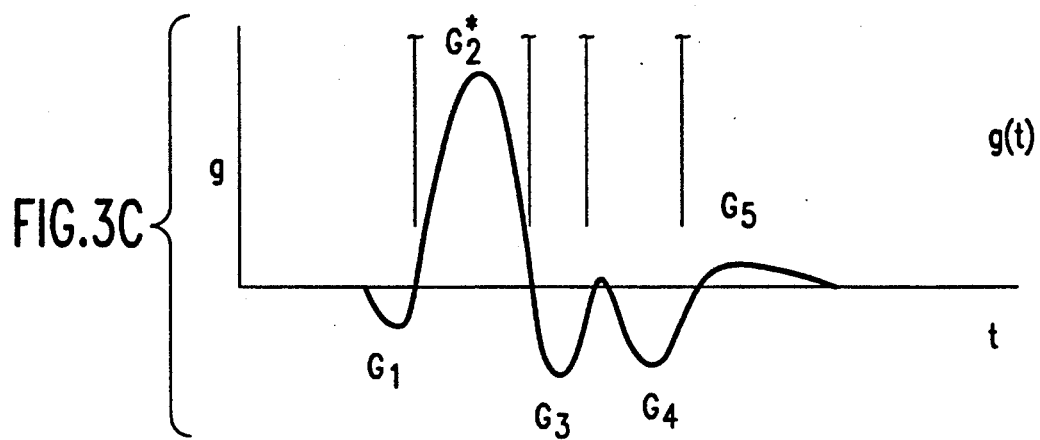

A typical cardiac biopotential comprises a series of complexes 14(1)–14(N), as shown in FIG. 3A. FIG. 3B illustrates a waveform f(t) representing a single complex 14 of the cardiac biopotential shown in FIG. 3A. FIG. 3C illustrates a waveform g(t) representing the processed version of f(t). The signal g(t) may be a derivative of the signal f(t), and in this regard, the signal processor 12 may take the derivative of an input signal. However, other signal processing techniques may be used for obtaining the waveform g(t).

Next in step 22, the feature values of the complex g(t) are determined. Specifically, the sequence of maximum positive and minimum negative values (feature values) are extracted from the complex g(t). In the diagram shown in FIG. 3C, the feature values are G1–G5. In addition, the feature value with the largest absolute value is at feature value G2 and is designated as such with an asterisk: G2*.

As briefly mentioned above, in actual practice, steps 20 and 22 are performed in two instances to generate two types of data. In the first instance, a cardiac biopotential complex is processed in step 20 and the sequence of maximum positive and minimum negative values are determined in step 22. In step 24, the complex is classified as a baseline complex or a non-baseline complex. This classification is based on the characteristic cycle length associated with the complex. The characteristic heart rate associated with the complex is the inverse of the characteristic cycle length associated with the complex. If the characteristic cycle length of the complex is greater than a threshold, then this "slow" complex is classified as a baseline complex. If the characteristic cycle length of the complex is less than or equal to the threshold, then this "fast" complex is classified as a non-baseline (tachycardiac) complex.

If in step 24, the complex is classified as a baseline complex, then in step 26 the complex is assigned, using the following clustering algorithm, to the first cluster (either the normal baseline cluster or one of up to eight abnormal baseline clusters) to which it is sufficiently similar in feature space. The cluster algorithm may be performed on a patient under supervision of a physician and under controlled conditions. However, the algorithm could also automatically process any baseline complexes during non-controlled conditions to update the baseline clusters. The objective of the clustering algorithm is to separate abnormal baseline complexes from normal baseline complexes. The term baseline is meant to include hemodynamic baseline or physiological baseline.

Cluster number one is the cluster to which the most complexes have been assigned, and by definition it is the normal baseline cluster. Associated with this cluster is its characteristic sequence of feature values: the sequence of feature values which are characteristic of the complexes assigned to it. Associated with each of the remaining, abnormal baseline clusters is the characteristic sequence of feature values determined from the complexes assigned to it.

For each cluster, the similarity feature value ($a_{\parallel}$) and the dissimilarity feature value ($a_{\perp}$) are calculated from the baseline complex's sequence of feature values and the cluster's characteristic sequence of feature values, analogous to the procedure for the classification of a non-baseline complex described in steps 28 to 38. If the condition ($0.8 < a_{\parallel} < 1.2$) and the condition ($0.0 \leq a_{195} < 0.2$) are true, then the baseline complex is sufficiently similar to this cluster and therefore is assigned to this cluster; 1.0 is added to this cluster's number of assigned complexes; and clustering stops. If the above conditions are not both true, clustering continues with an attempt to assign the baseline complex to the cluster which has the next most baseline complexes assigned to it.

When the baseline complex is finally assigned to a cluster, then each of the values of the complex's sequence is averaged with each of the corresponding values of the cluster's characteristic sequence to update the latter. If the baseline complex is not assigned to any cluster, the baseline complex defines a new cluster.

Since the complex is a baseline complex, in step 26, the VT baseline complex decrement value, 1.0, is subtracted from a VT discrimination counter, and the non-VT baseline complex decrement value, 1.0, is subtracted from a non-VT discrimination counter. Also, the clusters are sorted by the number of complexes assigned to them, so that cluster number one has the most complexes, cluster number two has the next most complexes, etc.

Thus, this clustering procedure effectively updates the characteristic sequence of feature values of the complexes of the normal baseline cluster whenever a complex is classified as a normal baseline complex in step 24. This on-going process continually adapts the characteristic sequence of feature values of the complexes of the normal baseline cluster to the patient's changing baseline morphology.

The assignment to a cluster of a baseline complex using the similarity feature value and the dissimilarity feature value calculated from the baseline complex's sequence of feature values and the cluster's characteristic sequence of feature values can be generalized. This generalization is analogous to the procedure described for the generalization, using a subspace spanned by a set of basis vectors, of the classification in steps 32 to 38 of a non-baseline complex.

In the analogy, the sequence of feature values for the baseline complex (event) in clustering is analogous to the non-baseline complex's sequence of feature values in classification, and the cluster's characteristic sequence of feature values in clustering is analogous to the normal baseline complexes' characteristic sequence of feature values in classification. Thus the baseline vector (or event vector) in clustering is analogous to the non-baseline vector in classification; the cluster vector in clustering is analogous to the normal baseline vector in classification; the cluster's subspace in clustering is analogous to the discrimination subspace in classification; and the cluster point of the baseline complex (event) in clustering is analogous to the discrimination point in classification. The baseline complex (event) is assigned to the first cluster for which the location of the cluster point of the baseline complex (event) is within one of the predetermined regions of the cluster's subspace.

This completes the description of the generalization, using a subspace spanned by a set of basis vectors, of the assignment to a cluster of a baseline complex.

The normal baseline cluster's complexes' characteristic feature value sequence can be written as, e.g., N1, N2*, N3, N4, where, e.g., N2* indicates that N2 is the feature value with the largest absolute value.

Similarly, in the second instance, a non-baseline sequence is obtained by processing a cardiac biopotential complex in step 20 and determining the feature values in step 22. Then, the cycle length of the complex is examined in step 24. If the complex is classified as a non-baseline complex, then it is tachycardiac, but of unknown type. The feature value sequence of this non-baseline complex can be written as, e.g., A1, A2, A3, A4*, A5, where, e.g., A4* indicates that A4 is the feature value with the largest absolute value for this sequence.

Next, in step 28, the feature value with the largest absolute value for the normal baseline's characteristic sequence and for the non-baseline sequence are designated as fiducial points. These two sequences of feature values are aligned so that the two fiducial points coincide in position, to create a first candidate aligned sequence pair. This is shown in FIG. 4 where the feature values N2* and A4* are aligned with each other.

Two m-dimensional vectors are then created in step 30 by filling zeros in either sequence of values for any missing entries, to create a first candidate baseline vector and non-baseline vector pair. This is shown in FIG. 5 in which the first candidate normal baseline vector N and the first candidate non-baseline vector A are created. In the example shown in FIG. 5, m=6. The value of m depends on the location of the feature value with the largest absolute value in each of the two sequences. Next, the magnitude of the vector difference (A−N) between the first candidate non-baseline vector A and the first candidate normal baseline vector N is calculated.

Next, in an analogous procedure, the normal baseline's characteristic sequence and the non-baseline sequence are aligned to each other such that the non-baseline sequence fiducial point is located one feature value to the right of the normal baseline's characteristic sequence fiducial point, to create a second candidate aligned sequence pair. Two m'-dimensional vectors are then created by filling zeros in either sequence of values for any missing entries, to create a second candidate baseline vector and non-baseline vector pair. The magnitude of the vector difference ($A_r - N_R$) between the second candidate non-baseline vector $A_r$ and the second candidate normal baseline vector $N_R$ is calculated.

Next, in yet another analogous procedure, the normal baseline's characteristic sequence and the non-baseline sequence are aligned to each other such that the non-baseline sequence fiducial point is located one feature value to the left of the normal baseline's characteristic sequence fiducial point, to create a third candidate aligned sequence pair. Two m''-dimensional vectors are then created by filling zeros in either sequence of values for any missing entries, to create a third candidate baseline vector and non-baseline vector pair. The magnitude of the vector difference ($A_L - N_L$) between the third candidate non-baseline vector $A_L$ and the third candidate normal baseline vector $N_L$ is calculated.

Of the three candidates pairs of vectors (A, N), ($A_R$, $N_R$), and ($A_L$, $N_L$), the candidate pair with the smallest magnitude of the vector difference is chosen to be the non-baseline vector A and the normal baseline vector N in step 31. This process provides robustness by accommodating a non-VT complex for which the non-baseline sequence fiducial point and the normal baseline's characteristic sequence fiducial point (first candidate pair) have opposite signs. In this situation the magnitude of the vector difference is large, so that the complex would be classified as a VT complex. Therefore the second candidate pair and the third candidate pair are also considered, since for each pair, features having the same sign are aligned, resulting in a smaller vector difference magnitude and thus increasing the likelihood of the complex being classified as a non-VT complex. Alternatively, if the fiducial points have identical signs, then the first candidate pair will have the smallest vector difference magnitude and therefore will be the candidate most likely to result in the complex being classified as a non-VT complex.

Next, in step 32, the two vectors of the chosen candidate pair are normalized by dividing each by the magnitude of the normal baseline vector |N|, creating two new vectors N/|N| and A/|N|.

Figure 6:
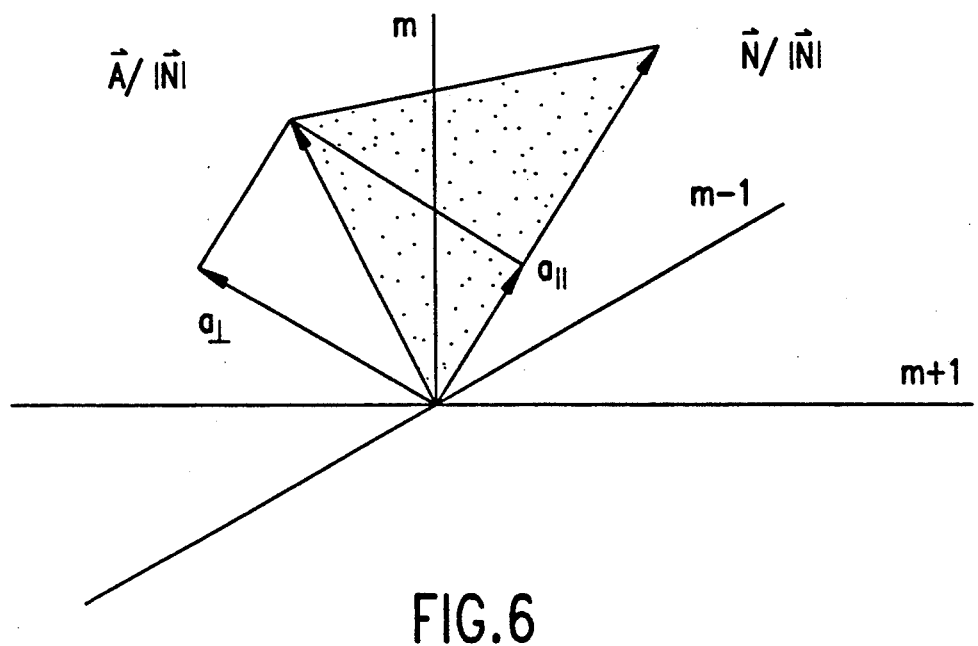
FIG. 6 is a graphical diagram illustrating the step of calculating the similarity and dissimilarity feature values in the discrimination plane, according to the discrimination algorithm of the present invention.

Conceptually, the vectors N/|N| and A/|N| define a two dimensional plane, as shown in FIG. 6. This two-dimensional plane, shown as a shaded surface between the vectors N/|N| and A/|N|, defines a discrimination plane.

The similarity and dissimilarity feature values are then calculated in step 34. Specifically, feature values designated $a_|$ and $a_\perp$ are the components of the vector A/|N| parallel and perpendicular, respectively, to the vector N/|N|. The component $a_|$ represents the degree with which the non-baseline vector A/|N| is similar to the normal baseline vector N/|N|. This value is obtained by taking the projection (dot product) of the vector A/|N| onto the vector N/|N|, which has unit length, as shown in FIG. 6. Thus, the feature value $a_|$ is the similarity feature of the vector A/|N| with respect to the vector N/|N|. The component $a_\perp$ represents the degree with which the non-baseline vector A/|N| is dissimilar to the normal baseline vector N/|N|. This value is obtained by taking the projection of the vector A/|N| onto the vector in the discrimination plane which has unit length, and which is perpendicular to the vector N/|N|, as shown in FIG. 6. Thus, the feature value $a_\perp$ is the dissimilarity feature of the vector A/|N| with respect to the vector N/|N|. Consequently, the comparison of the normal baseline complexes' characteristic feature value sequence and the non-baseline complex's feature value sequence is simplified from a complex multi-variate problem to a procedure involving only two feature values: $a_{s|}$ and $a_\perp$.

Figure 7:
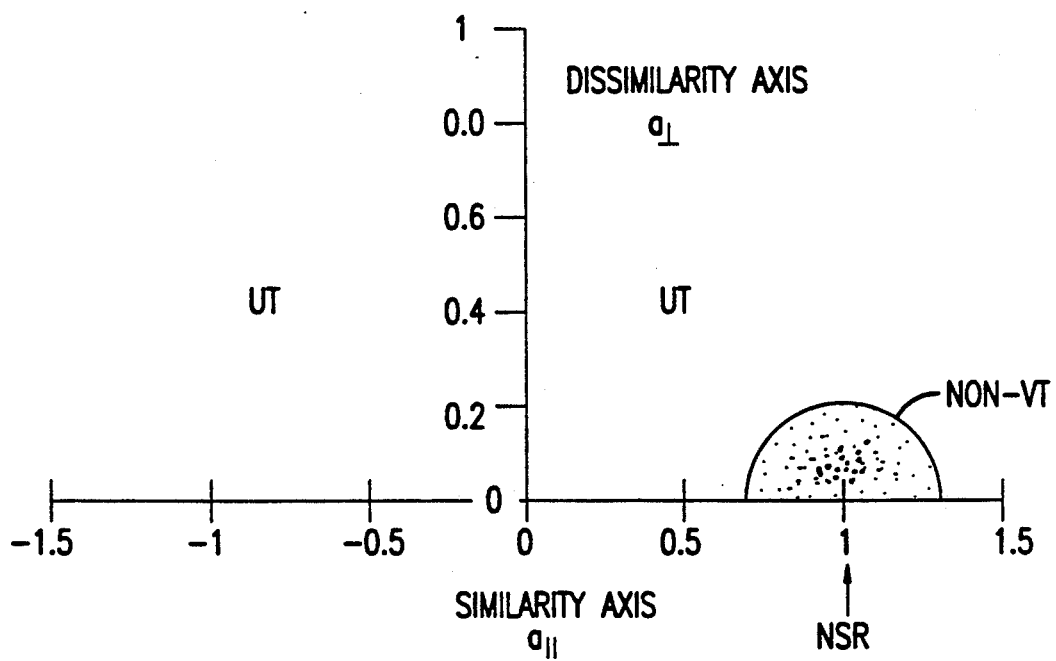
FIG. 7 is a graphical diagram illustrating the step of classifying the tachycardia and thus determining appropriate therapy based on the similarity and dissimilarity feature values.

Next, in step 36, the location in the discrimination plane of the feature values $a_|$ and $a_\perp$ for the non-baseline complex is examined to classify the complex as a VT complex or a non-VT complex. As shown in FIG. 7, coordinate axes are set up in the discrimination plane as orthogonal axes $a_|$ and $a_\perp$, also hereinafter referred to as the similarity and dissimilarity coordinate axes.

Classification of the non-baseline complex is determined by the location of the point, termed a discrimination point, having coordinates equal to the similarity and dissimilarity feature values ($a_|$, $a_\perp$) of the non-baseline complex's vector. Classification of the non-baseline complex is performed in step 38. If the discrimination point ($a_|$, $a_\perp$) falls within a predetermined small region surrounding the baseline point (1.0, 0.0), then the non-baseline complex is classified as a non-VT complex. The non-VT increment value, 1.0, is then added to the non-VT discrimination counter, and the VT decrement value, 0.5, is subtracted from the VT discrimination counter in step 40. Otherwise, if the discrimination point ($a_|$, $a_\perp$) falls outside of this region, the non-baseline complex is classified as a VT complex. Then, the VT increment value, 1.0, is added to the VT discrimination counter, and the non-VT decrement value, 0.5, is subtracted from, the non-VT discrimination counter in step 42. The boundary separating the non-VT and VT regions within the discrimination plane is predetermined by testing a population of patients, and does not change from individual to individual.

The classification of a non-baseline complex in terms of the similarity feature and the dissimilarity feature using the non-baseline vector A and the normal baseline vector N described above in steps 32 to 38 can be generalized, using a subspace spanned by a set of basis vectors, as follows.

First, a set is specified consisting of linearly independent vectors (not necessarily mutually orthonormal) which span (form a basis for) a subspace of the m-dimensional vector space of which the m-component non-baseline vector A and the m-component baseline vector N are elements. Next, the non-baseline vector A is projected on this subspace, thereby determining a linear combination of the basis vectors. Next, the values of the coefficients in this linear combination are calculated. These coefficients are the features used to classify the non-baseline complex using its associated non-baseline vector A.

Thus if $V_i$ (i=1, ..., k) are the k basis vectors which Awl span the subspace, then $$A = A_p + (A - A_p)$$

where by definition $A_p$ is the projection of A on the subspace:

$$A_p = \sum_{i=1}^{k} c_i \cdot v_i$$

where the scalar $c_i$ is the coefficient of $v_i$. For a basis vector $V_j$, $$V_j \cdot (A - A_p) = 0$$

by the definition of projection, where · is the dot product operator.
Thus, $$(v_j \cdot A) = \sum_{i=1}^{k} c_i * (v_j \cdot v_i) \quad (j = 1, \ldots, k)$$

These k equations can be solved for the k different coefficient values $c_i$ ($i = 1, \ldots k$).

These coefficients are the features used to classify the non-baseline complex using its associated non-baseline vector A, and the coefficient values are the feature values. Conceptually, the subspace spanned by the basis vectors defines a discrimination subspace.

Next, the location in the discrimination subspace of the point, termed a discrimination point, having coordinates equal to the coefficient values $c_i$ ($i = 1, \ldots, k$) for the non-baseline complex is examined to classify the complex as a VT complex or a non-VT complex. To effect this, basis vector coordinate axes are set up in the discrimination subspace in directions given by the basis vectors $v_j$ ($j = 1, k$). The origin of the discrimination subspace basis vector coordinate axes is located at the intersection of the basis vector coordinate axes. The location of the discrimination point is such that the position along each basis vector coordinate axis is at a coordinate relative to the origin equal to the basis vector coefficient value. If the discrimination point falls within certain predetermined regions of the discrimination subspace, then the non-baseline complex is classified as a non-VT complex. Otherwise, if the discrimination point falls outside these regions, the non-baseline complex is classified as a VT complex.

This completes the description of the generalization, using a subspace spanned by a set of basis vectors, of the classification of a non-baseline complex in steps 32 to 38.

Based on the classifications of previous non-baseline complexes, a determination is made in step 44 as to whether there is sufficient information to classify the tachycardia. That is, cardiac biopotentials are continuously sensed and processed. The sequences of feature values for additional non-baseline complexes are compared with the normal baseline's characteristic sequence in order to classify the tachycardia. Also, sequences of feature values for complexes which are sensed and are determined to be baseline update the characteristic sequence of feature values of the normal or abnormal baseline clusters.

The VT discrimination counter and the non-VT discrimination counter in step 44 are used to classify the tachycardia as VT or non-VT. The VT discrimination counter is initialized to the VT initial value, 0. The maximum allowed value is the maximum VT value, 20. Its minimum allowed value is the minimum VT value, 0. The non-VT discrimination counter is initialized to the non-VT initial value, 0. Its maximum allowed value is the maximum non-VT value, 20. Its minimum allowed value is the minimum non-VT value, 0.

If the VT discrimination counter value is greater than the VT absolute threshold value, 10, and if the VT discrimination counter value minus the non-VT discrimination counter value is greater than the VT relative threshold value, 0, then in step 46 the tachycardia is classified as VT, and VT therapy is prescribed. If the non-VT discrimination counter value is greater than the non-VT absolute threshold value, 10, and if the non-VT discrimination counter value minus the VT discrimination counter value is greater than the non-VT relative threshold value, 0, then in step 46, the tachycardia is classified as non-VT, and non-VT therapy is prescribed. If neither of those two sets of conditions is met, the method returns to step 20.

The small region surrounding the normal baseline point (1.0, 0.0) is predetermined heuristically as follows.

An estimate of the small region is made. Then the algorithm described above for discriminating VT and non-VT is executed using cardiac biopotentials of known type (baseline and VT or non-VT) obtained from a large population of patients. In each case, the known type of the tachycardia (VT or non-VT) is compared with the classification made by the discrimination counters in step 46. Then, if necessary, the small region is modified in such a way as to increase the agreement between the known types and the discrimination counter classifications. This procedure of modifying the small region is repeated until the agreement is optimized.

For example, for unipolar ventricular electrograms, the small region was determined to be the triangle defined by three points in the discrimination plane. The (similarity, dissimilarity) coordinate values of these points are (0.96, 0.0), (2.8, 0.0), and (1.76, 0.373).

The detailed description given above is intended by way of example only. It is not intended to limit the present invention to a sequence of feature values which are the sequence of maximum positive and minimum negative values of a complex in a processed cardiac biopotential or to a fiducial point defined as the feature value with the largest absolute value. Another possible example is the definition of the baseline and non-baseline m-dimensional vectors from the baseline and non-baseline sequences of m feature values, where the features are arbitrary. No fiducial identification is required if the first feature in the baseline sequence always corresponds to the first feature in the non-baseline sequence, etc. Moreover, the algorithm may be implemented without discriminating between normal baseline and abnormal baseline complexes.

Similarly, according to a second embodiment, for discriminating hemodynamically stable from unstable tachycardias, any signal or condition related to the hemodynamics of the heart (e.g., pressure, flow, and impedance/volume) could be sensed and processed in a manner similar to that of the cardiac biopotential of the first embodiment. In this case, a sequence of hemodynamic features is computed from each event of the signal. The characteristic cycle length associated with the event, which is the inverse of the characteristic rate associated with the event, is used to classify it as a hemodynamic baseline event or a hemodynamic non-baseline event. From the hemodynamic baseline events, a characteristic hemodynamic baseline sequence is obtained and updated. A hemodynamic non-baseline sequence is obtained from each hemodynamic non-baseline event. A hemodynamic discrimination point $(a_{\parallel}, a_{\perp})$ is determined from the non-baseline sequence and the characteristic baseline sequence. If the point is located in a predetermined hemodynamic small region surrounding the hemodynamic baseline point (1.0, 0.0) in the hemodynamic discrimination plane, then the hemodynamic non-baseline event is classified as "stable", otherwise, it is classified as "unstable". Stable and unstable hemodynamic discrimination counters are used to classify the tachycardia as hemodynamically stable or unstable, similar to the VT and non-VT discrimination counters, so that appropriate therapy can be specified.

In the second embodiment, the stable and unstable hemodynamic discrimination counters have associated therewith values termed: unstable hemodynamic initial value and stable hemodynamic initial value; maximum unstable hemodynamic value and maximum stable hemodynamic value; minimum unstable hemodynamic value and minimum stable hemodynamic value; unstable hemodynamic increment value and stable hemodynamic increment value; unstable hemodynamic decrement value and stable hemodynamic decrement value; unstable hemodynamic absolute threshold and unstable hemodynamic relative threshold; and finally stable hemodynamic absolute threshold and stable hemodynamic relative threshold. All of those are analogous to those values described with respect to the VT and non-VT discrimination counters in the first embodiment.

The predetermined hemodynamic small region is obtained by estimating a small region and then testing a population of patients each with a tachycardia known to be hemodynamically stable or unstable. The region is then modified in such a way as to optimize the agreement between the known types and the classifications made by the hemodynamic discrimination counters.

Furthermore, according to a third embodiment, the location of a physiological discrimination point $(a_{\parallel}, a_{\perp})$ can be used to determine the pacing rate required in a physiological multi-sensor rate adaptive pacing system. To this end, one or more features are extracted from each of several physiological sensors (e. g. , activity, flow, pressure, impedance, and electrograin) . Such physiological indicators are indicative of the hemodynamic performance required by a patient's physical activity. The numeric values for each of the above features are assumed to correlate significantly with the metabolic needs of the patient. In addition, the expected relationship between each feature value and "ideal" heart rate is predetermined. The feature values are extracted from the physiological sensed signals at events which may be aperiodic (e.g., per cardiac cycle, at QRS-complex, etc.) . During physiological baseline (resting) conditions, characteristic feature values are determined and a reference m-dimensional physiological baseline vector N containing the feature values is created. The location of a resulting physiological discrimination point in a physiological discrimination plane is associated with a predetermined ideal rate at which the heart should beat, for each event.

Preferably, the reference physiological baseline vector N adaptably changes on an event basis. In one implementation, each reference feature value is based on an output of an event-based low-pass filter with a large event constant. For example, the feature values could be averaged over 1,000 heart beats.

New feature values are determined using event-based processing; for example, values are computed every ten beats. Then, an m-dimensional physiological non-baseline vector A containing the new feature values for one event is created. The A and N vectors are compared. If the magnitude of the vector difference between A and N is less than a physiological threshold, A is used to update N. If the difference is greater than the physiological threshold, similarity and dissimilarity values are computed to determine the location of the physiological discrimination point on the physiological discrimination plane. The locations of a number of such points on the physiological discrimination plane determines the heart rate response value of the pacemaker. A physiological discrimination counter is incremented for mismatches between A and N, and decremented when the vectors nearly match. Heart rate is increased above physiological baseline only when the physiological discrimination counter exceeds a programmable number. Data for each event are accumulated, and an ideal pacing rate at which the pacemaker should be controlled to deliver pacing pulses to the heart is determined.

Other variations can be made such as using statistical classification methods rather than regions in the discrimination plane to automatically determine classification.

The discrimination algorithm of the present invention is implemented by software run on a microprocessor or computer. However, certain steps of the algorithm could be implemented by analog circuitry. In this regard, many feature values can be extracted from normal baseline and non-baseline complexes using analog circuitry which runs in parallel with the digital circuitry to reduce the digital computational requirements of the micro-processor. For example, the signal processing step 20 can be performed by analog switched-capacitor circuitry. The peak values (maximum positive and minimum negative) computed in step 22 may be determined with analog peak detectors. Steps 24, 26, 28 and 30 may be performed on a microcomputer using firmware. Steps 32–36 preferably are performed by a digital signal processing (DSP) chip. The classification decision in step 38 is preferably done by a microcomputer firmware. The discrimination counters may each comprise a eight-bit register or memory location within a microcomputer.

The above description is intended by way of example only and is not intended to limit the present invention in any way except as set forth in the following claims.

We claim:

1. A method for discriminating between tachycardias comprising the steps of:
   sensing a cardiac biopotential signal comprising consecutive biopotential complexes;
   determining a characteristic cycle length associated with each cardiac biopotential complex;
   designating a biopotential complex to be non-baseline if the characteristic cycle length is less than a predetermined threshold and otherwise designating the complex to be baseline;
   obtaining a characteristic sequence of feature values for cardiac biopotential complexes determined to be baseline for a particular patient;
   obtaining a sequence of feature values for each cardiac biopotential complex determined to be non-baseline for that patient;
   creating a baseline vector and creating non-baseline vectors from said characteristic sequence of feature values for complexes determined to be baseline and from each sequence of feature values for complexes determined to be non-baseline, respectively;
   comparing each of the non-baseline vectors with the baseline vector; and
   determining the type of tachycardia of a non-baseline complex based on the comparison of each non-baseline vector with the baseline vector.

2. The method of claim 1, and further comprising the step of accumulating comparison data related to the comparison of each of the non-baseline vectors with the baseline vector, and the step of determining the type of tachycardia based on the accumulated comparison data.

3. The method of claim 2, wherein said step of accumulating comparison date related to the comparison of each of the non-baseline vectors with the baseline vector comprises the steps of:
- initializing a VT discrimination counter to a VT initial value;
- initializing a non-VT discrimination counter to a non-VT initial value;
- limiting the maximum value of the VT discrimination counter to a maximum VT value;
- limiting the maximum value of the non-VT discrimination counter to a maximum non-VT value;
- limiting the minimum value of the VT discrimination counter to a minimum VT value;
- limiting the minimum value of the non-VT discrimination counter to a minimum non-VT value;
- adding a VT increment value to the VT discrimination counter value and subtracting a non-VT decrement value from the non-VT discrimination counter when a complex is determined to be a non-baseline VT complex;
- adding a non-VT increment value to the non-VT discrimination counter and subtracting a VT decrement value from the VT discrimination counter when a complex is determined to be a non-baseline non-VT complex; and
- subtracting the VT baseline complex decrement value from the VT discrimination counter and subtracting the non-VT baseline complex decrement value from the non-VT discrimination counter when a complex is determined to be a baseline complex.

4. The method of claim 3, wherein said step of determining the type of tachycardia based on the accumulated comparison data comprises the steps of:
- determining the type of tachycardia to be VT when the VT discrimination counter value is greater than a VT absolute threshold value, and the VT discrimination counter value minus the non-VT discrimination counter value is greater then a VT relative threshold value; and
- determining the type of tachycardia to be non-VT when the non-VT discrimination counter value is greater than a non-VT absolute threshold value, and the non-VT discrimination counter value minus the VT discrimination counter value is greater than a non-VT relative threshold value.

5. The method of claim 1, wherein said step of obtaining a characteristic sequence of feature values for complexes determined to be baseline comprises the steps of:
- creating event vectors and cluster vectors from the sequence of feature values for each complex designated baseline and from the characteristic sequence of feature values associated with each cluster of like baseline complexes, respectively;
- comparing each event vector with each cluster vector;
- assigning the baseline complex to a cluster based on the comparison of each event vector with each cluster vector;
- defining a new cluster-by a baseline complex which cannot be assigned to any existing cluster;
- calculating an average of the corresponding components of said event vector and the cluster vector for the baseline complex and the cluster to which the baseline complex is assigned to obtain an updated characteristic sequence of feature values for said cluster;
- sorting the clusters in descending order of the number of events assigned to each cluster; and
- defining cluster number one, the cluster to which the most complexes are assigned, to be the normal baseline cluster.

6. The method of claim 5, wherein said step of creating each event vector and each cluster vector comprises the steps of:
- identifying and designating a feature value within each of said sequence of feature values for said baseline complex and said characteristic sequence of feature values for said cluster as fiducial points for the respective sequences;
- aligning said baseline complex sequence and said cluster characteristic sequence to each other according to the respective fiducial points; and
- adding or removing feature values at the ends of said baseline complex sequence and said cluster characteristic sequence to create said event vector and said cluster vector such that the vectors have equal numbers of components and such that corresponding components are occupied by feature values.

7. The method of claim 6, wherein said step of adding feature values at the ends of said baseline complex sequence and said cluster characteristic sequence comprises the step of filling in zeros to sequence positions which are not occupied by feature values.

8. The method of claim 6, wherein said step of identifying and designating a fiducial point for a sequence comprises the step of identifying and designating the feature value with largest absolute value in the sequence.

9. The method of claim 5, wherein said step of comparing each event vector with each cluster vector comprises the steps of:
- specifying a set of linearly independent basis vectors which span a subspace of an m-dimensional vector space of which an m-component event vector and an m-component cluster vector are elements;
- projecting said event vector on said subspace, thereby determining a linear combination of said basis vectors;
- calculating the values of the coefficients in said linear combination; and
- designating the coefficient associated with each basis vector in said linear combination to be the basis vector's coefficient.

10. The method of claim 9, wherein said step of assigning comprises the steps of:
- designating said subspace spanned by said basis vectors to be said cluster's subspace;
- defining for each of said basis vectors of said cluster's subspace a basis vector coordinate axis with the origin of said cluster's subspace being located at the intersection of said basis vector coordinate axes;
- designating certain regions in said cluster's subspace as regions particular to baseline complexes assigned to said cluster;
- locating for each baseline complex a cluster point in said cluster's subspace, the coordinates of said cluster point defined by said basis vectors' coefficients so that the position of said cluster point along each basis vector coordinate axis is at a coordinate relative to the origin equal to said basis vector coefficient value; and assigning each baseline complex to the first cluster for which the location of said cluster point of the baseline complex is within one of said regions particular to said cluster.

11. The method of claim 5, wherein the baseline vector is a normal baseline vector created on the basis of the characteristic sequence of feature values for said normal baseline cluster.

12. The method of claim 1, wherein said step of creating the baseline vector and each non-baseline vector comprises the steps of:

identifying and designating a feature value within each of said characteristic baseline sequence and said non-baseline sequence as a fiducial point for the respective sequences;

creating candidate aligned sequence pairs from said characteristic baseline sequence and non-baseline sequences;

creating from each candidate aligned sequence pair a candidate baseline vector and non-baseline vector pair; and selecting a candidate baseline vector and non-baseline vector pair as the baseline vector and the non-baseline vector.

13. The method of claim 12, wherein said step of creating a candidate aligned sequence pair comprises the step of aligning said characteristic baseline sequence and non-baseline sequence according to their respective fiducial points to create said candidate aligned sequence pair.

14. The method of claim 12, wherein said step of creating candidate aligned sequence pairs comprises the steps of:

aligning said characteristic baseline sequence and non-baseline sequence according to their respective fiducial points to create a first candidate aligned sequence pair;

aligning said characteristic baseline sequence and non-baseline sequence to each other such that said non-baseline sequence fiducial point is located one feature value to the right of said characteristic baseline sequence fiducial point to create a second candidate aligned sequence pair; and aligning said characteristic baseline sequence and non-baseline sequence to each other such that said non-baseline sequence fiducial point is located one feature value to the left of said characteristic baseline sequence fiducial point to create a third candidate aligned sequence pair.

15. The method of claim 12, wherein said step of creating a candidate baseline vector and non-baseline vector pair from each candidate aligned sequence pair comprises the step of adding or removing feature values at the ends of said characteristic baseline sequence and non-baseline sequence comprising said candidate aligned sequence pair to create said candidate baseline vector and non-baseline vector pair such that said vectors have equal numbers of components and such that corresponding components are occupied by feature values.

16. The method of claim 15, wherein said step of adding feature values at the ends of said characteristic baseline sequence and non-baseline sequence comprises the step of filling in zeros to sequence positions which are not occupied by feature values.

17. The method of claim 12, wherein said step of selecting a candidate baseline vector and non-baseline vector pair as the baseline vector and non-baseline vector comprises the steps of:

calculating the magnitude of the vector difference between said baseline vector and non-baseline vector comprising each candidate pair; and selecting the candidate pair with the smallest magnitude of vector difference as the baseline vector and non-baseline vector.

18. The method of claim 12, wherein said step of identifying and designating a fiducial point for a sequence comprises the step of identifying and designating a feature value with largest absolute value in the sequence.

19. The method of claim 1, wherein said step of comparing comprises the steps of:

normalizing said baseline vector and said non-baseline vector by dividing by the magnitude of the baseline vector thereby creating a normalized baseline vector and a normalized non-baseline vector;

calculating a similarity feature value of said normalized non-baseline vector with respect to said normalized baseline vector by determining the projection of said normalized non-baseline vector onto said normalized baseline vector; and calculating a dissimilarity feature value of said normalized non-baseline vector with respect to said normalized baseline vector by determining the projection of said normalized non-baseline vector onto an axis in the plane defined by the normalized baseline vector and the normalized non-baseline vector which is perpendicular to said normalized baseline vector.

20. The method of claim 19, wherein said step of determining the type of tachycardia of a non-baseline complex comprises the steps of:

defining a discrimination plane having a similarity coordinate axis and a dissimilarity coordinate axis which is orthogonal to said similarity coordinate axis, the origin of said discrimination plane being located at an intersection of said similarity coordinate axis and said dissimilarity coordinate axis;

designating certain regions in said discrimination plane as regions particular to certain tachycardias;

locating for each non-baseline complex a discrimination point in said discrimination plane, the coordinates of said discrimination point defined by said similarity feature value and said dissimilarity feature value so that the position of said discrimination point is along said similarity axis at a rectangular coordinate relative to the origin equal to said similarity value and along said dissimilarity axis at a rectangular coordinate relative to the origin equal to said dissimilarity value; and determining the type of tachycardia of the non-baseline complex based on the location of said discrimination point in said discrimination plane.

21. The method of claim 1, wherein said step of comparing comprises the steps of:

specifying a set of linearly independent basis vectors which span a subspace of an m-dimensional vector space of which an m-component non-baseline vector and an m-component baseline vector are elements;

projecting said non-baseline vector on said subspace thereby determining a linear combination of said basis vectors;

calculating the values of the coefficients in said linear combination; and terming the coefficient associated with each basis vector in said linear combination to be the basis vector's coefficient.

22. The method of claim 21, wherein said step of determining the type of tachycardia of a non-baseline complex comprises the steps of:

designating said subspace spanned by said basis vectors to be a discrimination subspace;

defining for each of said basis vectors of said discrimination subspace a basis vector coordinate axis with the origin of said discrimination subspace being located at the intersection of said basis vector coordinate axes;

designating certain regions in said discrimination subspace as regions particular to certain tachycardias;

locating for each non-baseline complex a discrimination point in said discrimination subspace, the coordinates of said discrimination point defined by said basis vectors' coefficients so that the position of said discrimination point along each basis vector coordinate axis is at a coordinate relative to the origin equal to said basis vector coefficient value; and determining the type of tachycardia of the non-baseline complex based on the location of said discrimination point in said discrimination subspace.

* * * * *